United States Patent [19]

Blank et al.

[11] 3,957,740
[45] May 18, 1976

[54] COPOLYMERS
[75] Inventors: Izhak Blank; Joseph Fertig, both of Haifa, Israel
[73] Assignee: Hydrophilics International, Inc., New York, N.Y.
[22] Filed: July 24, 1974
[21] Appl. No.: 491,535

Related U.S. Application Data
[63] Continuation-in-part of Ser. No. 246,831, April 24, 1972, abandoned.

[52] U.S. Cl. ............................... 526/16; 260/2 EN; 264/1; 351/160; 424/195; 526/50; 526/317
[51] Int. Cl.$^2$.................... C08F 8/30; C08F 220/06
[58] Field of Search......... 260/86.1 R, 80.72, 80.73, 260/2 EN, 29.6 TA, 29.6 MN, 80.8

[56] References Cited
UNITED STATES PATENTS

| | | |
|---|---|---|
| 3,261,797 | 7/1966 | McDowell et al. ........... 260/29.6 TA |
| 3,678,013 | 7/1972 | Minckler......................... 260/77.5 R |
| 3,787,378 | 1/1974 | Blank.............................. 260/86.1 R |

*Primary Examiner*—John Kight, III
*Attorney, Agent, or Firm*—Ryder, McAulay, Fields, Fisher & Goldstein

[57] ABSTRACT

Copolymers comprising acrylic or methacrylic acid and methyl methacrylate are neutralized by the addition of cyclic alkylene imines, preferably ethylene imine, to form a product which is capable of absorbing large amounts of material soluble in water, and slowly releasing those materials. The fundamental copolymer may be modified by the addition of cross-linking agents, chain terminators, plasticizers, etc., prior to treatment with the alkylene imine. The treated copolymers are particularly useful in the formation of contact lenses for the application of medicinals to the eye, and for other depot materials.

5 Claims, No Drawings

＃ COPOLYMERS

CROSS-REFERENCES TO RELATED APPLICATIONS

This application is a continuation-in-part of our copending application, Ser. No. 246,831 for "Copolymers," filed April 24, 1972, now abandoned.

This application is related to the copending applications of Izhak Blank, Ser. No. 139,545 for "Optical Contact Lenses and Related Devices," filed May 3, 1971, now U.S. Pat. No. 3,728,317, and Ser. No. 139,544 for "Chemical Composition for Viscosity Control and Film Forming Materials," filed May 3, 1971, now U.S. Pat. No. 3,728,314, in that similar materials are copolymerized and neutralized to form hydrophilic copolymers.

This application is based upon copending British Application No. 37,936/71 for "Copolymers and Compositions Containing Copolymers," filed Aug. 12, 1971 and the filing date of that application is claimed.

BACKGROUND OF THE INVENTION

Previously referenced U.S. Pat. No. 3,728,317 describes the formation of a hydrophilic copolymer, primarily for use in contact lenses. The basic components of that copolymer are methyl methacrylate and acrylic acid which are copolymerized and subsequently neutralized with a basic material, such as ammonium hydroxide. The application also discloses that various medicinal agents can be absorbed by the resulting copolymer, or the copolymer in the form of a lens, for application of that medicinal to the eye. While the neutralized copolymer described and claimed in the application is entirely adequate for the purposes set forth, it does not provide a slow, controlled release of the medicinal and, further, cannot be employed when the medicinal to be absorbed is acidic in nature, i.e., has a pH less than 7.

Many active medicinal materials are most stable in the acid form. It is frequently desired that these medicinals be applied for a sustained period with a single physical application.

If a polymer formed according to the disclosure of the copending application, now U.S. Pat. No. 3,728,317, is treated with a material under acidic conditions, it will not hydrate. If the polymer has already been hydrated with sodium hydroxide, ammonium hydroxide, or some other basic solution and is then put in contact with an acidic solution, the resulting materials shrinks and hardens. Thus, it can be seen that such a material is not useful with acidic active agents.

Thus, to adequately treat a patient with an active medicinal of this type, there are two requirements for the carrier. The first requirement is that the carrier be stable in and capable of absorbing in an acid medium, while still retaining its softness. It is also desirable that the material should be functional in neutral and alkaline media. The second requirement is that the carrier slowly release the medicinal and not release the major portion of it immediately upon application. In some instances, particularly as in treatment of the eye, a third critical factor exists. That third factor is that the carrier must be comfortable and, more particularly, soft and flexible. None of the products of the prior art are capable of meeting each of these criteria.

The capability of absorbing and releasing various materials can be enhanced by introducing hydrophilic cross-linking agents, such as polyethylene glycol dimethacrylate, maleates, etc. These cross-linking agents tend to produce a softer final product, while the use of other cross-linking agents, such as divinylbenzene and dimethacrylate alkyl esters, tend to give much harder materials.

SUMMARY OF THE INVENTION

In accordance with the present invention, acrylic or methacrylic acid, or a mixture of the two, and methyl methacrylate or methyl acrylate are copolymerized in any standard manner. It is particularly preferable that this copolymerization be carried out, either in the presence of a chemical catalyst or by free ion polymerization, in bulk. Employing bulk copolymerization significantly improved and unique properties are obtained, as more fully set forth in the copending application, now U.S. Pat. No. 3,728,317, previously referred to.

The copolymer may have incorporated therein small amounts of internal plasticizers or chain terminators. The internal plasticizers are long chain acrylate or methacrylate esters, such as those having from 8 to 18 carbon atoms. Various thiols have been found particularly useful in chain termination, when this is desired.

After formation of the desired copolymer, it is treated with an aqueous solution of ethylene imine to neutralize the acid groups present in the copolymer. A variety of materials can be absorbed or adsorbed by the treated copolymer for subsequent, slow sustained release.

One material for which the cross-linked copolymer of the present invention is particularly valuable is pilocarpine hydrochloride, a medicinal for treatment of certain eye disorders.

DESCRIPTION OF THE PREFERRED EMBODIMENTS

In accordance with the present invention, a copolymer is first formed with from 10 to 30 parts, by volume, acrylic or methacrylic acid and from 50 to 90 parts, by volume, of a lower alkyl acrylate or methacrylate. By lower alkyl is meant an acrylate or methacrylate wherein the alkyl group has from 1 to 4 carbon atoms, such as methyl, ethyl, propyl, isopropyl, butyl, etc. The preferred amounts of acrylic or methacrylic acid are from 15 to 25 parts, by volume, while the preferred amounts of the lower alkyl acrylate or methacrylate are from 75 to 85 parts.

While the copolymer can be formed by suspension or emulsion polymerization, the polymerization is most preferably carried out in bulk. When bulk copolymerization is employed, the polymerization is carried out at a temperature of from 40° to 60°C., preferably from 45° to 55°C.

The polymerization is generally carried out in the presence of a suitable catalyst. Useful catalysts include peroxides, for example, benzoyl or lauryl peroxide, or an azo compound. The preferred catalyst is $\alpha,\alpha'$-azodiisobutyronitrile. When such chemical catalysts are employed, amounts of from 0.01 to 0.12% by weight, based upon the total weight of monomer, is generally employed. Preferably, the amount of catalyst is from 0.03 to 0.05%. The polymerization can be carried out in the presence of ultraviolet radiation.

In some instances, it may be desirable to internally plasticize the copolymer. Such internal plasticization is accomplished by copolymerizing a long chain ester of acrylic or methacrylic acid. By long chain is meant an ester of acrylic or methacrylic acid where the alkyl group has from 8 to 18 carbon atoms. A preferred plasticizer of this type is ethyl hexyl acrylate. Other plasticizers which may be used include lauryl acrylate, lauryl mthacrylate, stearyl acrylate, stearyl methacrylate, and similar materials. The amount of plasticizing monomer which is copolymerized can vary from 5 to 20 parts, by volume, preferably from 10 to 15 parts, by volume.

If desired, a chain terminator or regulator may be included in the copolymerization formula. The molecular weight of the material can be controlled in this way. A suitable chain terminator is dodecanethiol which can be employed in amounts of from 0.1 to 1.0%, by volume. Other suitable regulators include trichlorethylene and other materials known to the art.

The copolymers formed according to this invention can have a very high molecular weight, for example, more than 1,000,000 and often more than 2,000,000. The molecular weight can be determined by measuring the intrinsic viscosity of the formed copolymer in methyl ethyl ketone at 25°C. The copolymers of the present invention generally have intrinsic viscosities of at least 2.5.

Subsequent to formation of the copolymer, which may take place in a casting cell, the copolymer is treated with an aqueous solution of ethylene imine or a substituted ethylene imine. These materials are selected from those having the formula:

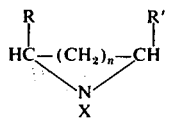
(1)

where R and R' are individually selected from the class consisting of hydrogen and lower alkyl radicals, X is hydrogen or hydroxyl, and $n$ is a number from 0 to 4. The preferred materials are those where $n$ is O, R and R' are hydrogen, methyl, or ethyl, and X is hydrogen. Most preferably, the material is ethylene imine.

The copolymer is immersed in an aqueous solution of the alkylene imine for from about 12 to 48 hours. Preferably, the copolymer is in a solid form when immersed, for example, in the form of a lens. While the reaction will proceed at ambient temperature, higher temperatures can be successfully employed.

The concentration of alkylene imine should be from about 0.5 to 5.0%, and sufficient alkylene imine should be allowed to react so as to neutralize essentially all of the acid groups on the copolymer.

While not wishing to be bound by theory, it is believed that, when using ethylene imine, the initial reaction product is the imonium salt of formula:

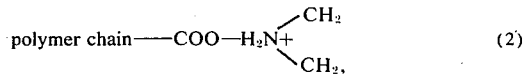
(2)

which produces a large hydration. The imonium salt is believed to be slowly transformed into the amino ethyl ester, with a resultant reduction in hydration, the ester having the formula:

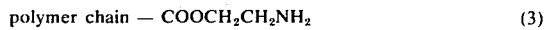
(3)

It is believed that the final form of the copolymer is an internal salt of the amine of formula (3) formed with an adjacent carboxylic group from the polymer chain and having the formula

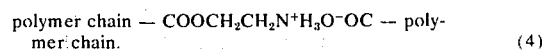
(4)

Treated copolymers formed as just described swell in both acidic and alkaline solutions. For example, a lens having 15% acrylic acid, and 85% methyl methacrylate, neutralized by treatment with a 1% aqueous solution of ethylene imine for 48 hours at ambient temperature, resulting in neutralization of essentially all of the copolymer acid groups, swelled in both acidic and alkaline solutions. A contact lens form was made from this cross-linked copolymer and when treated with a 0.36% hydrochloric acid solution achieved a hydration of 78%. The materials were optically clear and soft. Additionally, they absorbed essentially the same amounts of a medicinal agent, such as pilocarpine hydrochloride, as a hydrophilic copolymer which has not been treated with alkaline imine. However, the treated copolymers release the medicinal agent at a much slower rate, so as to provide for a sustained treatment with the material.

In order that those skilled in the art may be better enabled to practice the present invention, the following examples are given. These examples should be considered as illustrative only and not as limiting in any way the full scope of the invention as covered in the appended claims. All parts in these examples are by volume, unless otherwise indicated.

In some of the examples, there is a treatment with Sorensen's solution. This solution is formed by dissolving 3.40 grams potassium dihydrogen phosphate and 3.55 grams disodium hydrogen phosphate in water, and diluting to 1 liter.

Example 1

In this example a variety of materials were formed outside of the present invention. Such materials include hydrophilic lenses formed of acrylic or methacrylic acid and methyl methacrylate neutralized with sodium hydroxide, and similar copolymers cross-linked with materials other than ethylene imine. After formation of the copolymer with the compositions as indicated, the material was cut into discs of approximately 0.3 mm. thickness or lenses of approximately 0.15 mm. thickness, were hydrated in a 0.5% sodium hydroxide solution, were conditioned in Sorensen's solution, and were then treated with 0.3% pilocarpine hydrochloride in Sorensen's solution until constant weight was achieved. The rate of removal of the pilocarpine hydrochloride was then measured by placing the thus treated lens into 20 milliliters of Sorensen's solution and removing 2 milliliter aliquots of the solution at 5 minute intervals. The pilocarpine content was measured at 215 millimicrons on a Perkin-Elmer Hitachi 124 U.V. spectrophotometer. The aliquot was then returned to the bulk solution. The composition of the material, hydration, and concentration factor are shown in Table 1. The release rate of the pilocarpine hydrochloride for each copolymer is as indicated in Table 2.

Table 1

| Polymer | Methyl Methacrylate | Acrylic Acid | Hydration in 0.5 % NaOH (%) | Hydration in Sorensen's Solution (%) | Hydration in 0.3% Pilocarpine Hydrochloride Sorensen's Solution (%) | Milligrams Pilocarpine Absorbed Per Milligram Polymer | Concentration Factor |
|---|---|---|---|---|---|---|---|
| A | 87.5 | 12.5 | 67 | 59 | 52 | 0.056 | 17.3 |
| B | 86.5 | 13.5 | 75 | 69 | 63 | 0.064 | 12.7 |
| C | 85 | 15 | 76 | 72 | 62 | 0.077 | 15.8 |
| D | 80 | 20 | 88 | 89 | 87 | 0.080 | 4 |
| E | 75 | 25 | 91 | 92 | 90 | 0.080 | 3.5 |
| F | 85 | 15[1] | 74 | 62 | 50 | 0.064 | 21 |
| G | 82 | 15[2] | 66 | 56 | 47 | 0.075 | 26.53 |
| H | 80 | 15[3] | 58 | 47 | 36 | 0.064 | 35.8 |
| I | 82 | 15[4] | 64 | 52 | 47 | 0.069 | 25.2 |
| J | 80 | 15[5] | 59 | 46 | 43 | 0.086 | 37.8 |
| K | 75 | 15[6] | 48 | 32 | 31 | 0.093 | 68.5 |
| L | 82 | 15[7] | 81 | 78 | 74 | 0.053 | 6.25 |
| M | 80 | 15[8] | 77 | 69 | 65 | 0.069 | 12.4 |
| N | 75 | 15[9] | 82 | 80 | 77 | 0.070 | 7.1 |
| O | 75 | 20[10] | 64 | 60 | 50 | 0.072 | 20.2 |
| P | 75 | 15[11] | 85 | 84 | 82 | 0.060 | 4.3 |

[1] methacrylic acid
[2] also contains 3% ethylene glycol dimethacrylate
[3] also contains 5% ethylene glycol dimethacrylate
[4] also contains 3% polyethylene glycol 200 dimethacrylate
[5] also contains 5% polyethylene glycol 200 dimethacrylate
[6] also contains 10% polyethylene glycol 200 dimethacrylate
[7] also contains 3% carbowax 350 dimethacrylate
[8] also contains 5% carbowax 350 dimethacrylate
[9] also contains 10% carbowax 350 dimethacrylate
[10] also contains 5% polyethylene glycol 200 dimethacrylate
[11] also contains 10% polyethylene glycol 1500 dimaleate Concentration factor, as used in the table, refers to the amount of the medicinal agent which is absorbed, compared to that which might be absorbed. For example, if a 100 gram sample of the copolymer was immersed in a 1% pilocarpine hydrochloride solution, and increased in weight by 100 grams, it would be expected that 1 gram of pilocarpine hydrochloride would have been absorbed. If, on the other hand, with the same 100 gram increase in weight, 5 grams of pilocarpine hydrochloride are absorbed, then the concentration factor is 5.

Table 2

Release of Pilocarpine Hydrochloride Per Minute

|  | 50% | 75% | 100% |
|---|---|---|---|
| A | 2 | 4 | 22.5 |
| B | 2 | 3 | 25 |
| C | 2.5 | 6.5 | 21.5 |
| D | 14 | 45 | 140 |
| E | 10 | 28 | 150 |
| F | 2.5 | 4 | 38 |
| G | 6.5 | 10.5 |  |
| H | 3.5 | 7.5 | 29 |
| I | 3 | 9 | 43 |
| J | 6 | 15 | 78 |
| K | 20 | 60 | 137 |
| L | 2 | 4 | 78 |
| M | 3.5 | 6 | 78 |
| N | 2 | 4 | 110 |
| O | 14 | 40 | 150 |
| P | 10 | 31 | 60 |

Those copolymers which were cross-linked with carbowax 350 dimethacrylate had a good retention of pilocarpine hydrochloride, as can be seen from the table, and were soft. However, their retention rates were not sufficiently high as can be seen from the rapid release. The lenses made with polyethylene glycol 200 dimethacrylate, such as that made with 10%, did have a high absorption of pilocarpine hydrochloride and released it relatively slowly, but the lenses were hard. This can be seen from the low liquid content.

Example 2

In this example, a series of copolymers were treated with a 1% solution of ethylene imine for 24 to 48 hours until constant weight was achieved. Subsequently, the lenses were immersed in a 0.3% solution of pilocarpine hydrochloride in Sorensen's solution for 24 to 48 hours until a constant weight was achieved. The rate of removal of the pilocarpine hydrochloride was then measured by placing the thus treated lens into 20 millimeters of Sorensen's solution and removing 2 milliliter aliquots of the solution at 5 minute intervals. The pilocarpine hydrochloride content was measured at 215 millimicrons on a Perkin-Elmer Hitachi 124 U.V. spectrophotometer. The aliquot was then returned to the bulk solution. The compositions of these copolymers are given in Table 3 below. The release rate of the pilocarpine hydrochloride for each of these copolymers is shown in Table 4.

Table 3

| Copolymer | Methyl Methacrylate % By Volume | Acrylic Acid % By Volume | % Weight Increase in 1% Ethylene Imine | % Weight Increase In Sorensen's Solution | % Weight Increase in Pilocarpine Hydrochloride-Sorensen's Solution | Milligrams Pilocarpine Hydrochloride Per Milligram Polymer |
|---|---|---|---|---|---|---|
| Q | 85 | 15 | 58 | 50 | 50 | 0.023 |
| R | 80 | 20 | 63 | 58 | 58 | 0.026 |
| S | 75 | 25 | 68 | 63 | 60 | 0.026 |
| T | 82 | 15[7] | 48 | 50 | 47 | 0.027 |

Table 3-continued

| Copolymer | Methyl Methacrylate % By Volume | Acrylic Acid % By Volume | % Weight Increase in 1% Ethylene Imine | % Weight Increase In Sorensen's Solution | % Weight Increase in Pilocarpine Hydrochloride-Sorensen's Solution | Milligrams Pilocarpine Hydrochloride Per Milligram Polymer |
|---|---|---|---|---|---|---|
| U | 80 | 15[8] | 52 | 51 | 47 | 0.026 |
| V | 75 | 15[9] | 48 | 45 | 41 | 0.027 |
| W | 75 | 20[10] | 44 | 49 | 52 | 0.028 |
| X | 75 | 15[11] | 48 | 50 | 47 | 0.024 |

[7]also contains 3% carbowax 350 dimethacrylate
[8]also contains 5% carbowax 350 dimethacrylate
[9]also contains 10% carbowax 350 dimethacrylate
[10]also contains 5% polyethylene glycol 200 dimethacrylate
[11]also contains 10% polyethylene glycol 1500 dimaleate

Table 4

Release of Pilocarpine Hydrochloride in Hours

|   | 50% | 75% | 100% |
|---|---|---|---|
| Q | 48 | 72 | 90 |
| R | 48 | 72 | 82 |
| S | 48 | 72 | 80 |
| T | 48 | 70 | 94 |
| U | 60 | 84 | 90 |
| V | 48 | 68 | 78 |
| W | 48 | 72 | 80 |
| X | 40 | 72 | 96 |

Of the lenses referred to in Table 3, those formed from copolymers R and S were found to be soft. Lenses from Copolymers Q, U, W and X were found to be semi-soft, while lenses from copolymers T and V were found to be hard. As can clearly be seen from Table 4, the treatment of the copolymer with ethylene imine significantly increases the time required to release the pilocarpine hydrochloride. The maximum time for release, as indicated in Table 2 without ethylene imine treatment is no more than 2-½ hours. On the other hand, the minimum time for release of 50%, when similar copolymers are treated with ethylene imine, is 40 hours. Thus, the time of release is increased by a factor of at least 20. As previously indicated, such a long period of sustained release is particularly desired when medicinals of this type are to be released.

Example 3

A copolymer sheet containing 85% methyl methacrylate and 15% acrylic acid, 0.5mm thick, was immersed in a 1% aqueous solution of ethylenimine for one week at room temperature. A highly flexible hydrated sheet of good strength was obtained, which, after washing with distilled water, contained 50% water.

Example 4

A sheet of Example 3 was washed in distilled water, dried, and a section weighing 0.5gr was placed in a 0.3% solution of acetylsalicylic acid in saline solution. After 18 hours the section was removed, now weighing 1.0gr, and was then placed in 50ml saline. The release of acetylsalicylic acid into the saline solution was then followed by a measurement with a UV Spectrophotometer at 275 m$\mu$. It was found that the concentration of acetylsalicylic acid in the sheet was 20 times that of the solution. 50% of the acid was released in 30 minutes and 100% in four hours.

Example 5

A copolymer sheet containing 80% methyl methacrylate, 16% methacrylic acid and 4% ethyleneglycol dimethacrylate, 0.3mm thick, was immersed in a 1% solution of N-hydroxyethyl ethylenimine for one week at room temperature. A strong, flexible, hydrated sheet was obtained, which could be cut into various shapes.

Example 6

A copolymer sheet containing 75% methyl methacrylate, 15% acrylic acid and 10% 2-ethylhexylacrylate, 1mm thick, was immersed in a 2% solution of propylenimine for 1 week, giving a strong, flexible, hydrated sheet. Thin needles were cut from this sheet and thoroughly washed in distilled water. A needle weighing 7mg was then immersed in 0.5ml of a solution containing 250 units per millitier radioactive Insulin for 24 hours. It was found, using a Geiger counter, that the needle had absorbed 40% of the total available Insulin in the solution, and upon continuous immersion in saline solution (changed daily), released 25% of the Insulin within 14 days.

We claim:

1. A copolymer comprising from 10 to 30 parts, by volume, of a member selected from the class consisting of acrylic and methacrylic acid and from 50 to 90 parts by volume of a member selected from the class consisting of lower alkyl acrylate and methacrylate, said copolymer having been formed by bulk copolymerization to a molecular weight of more than 1,000,000, essentially all of the acids groups of said copolymer having been neutralized with an alkylene imine having the formula:

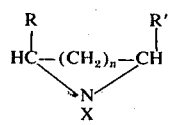

where R and R' are each selected from the class consisting of hydrogen and lower alkyl radicals, X is hydrogen or hydroxyl, and $n$ is a number from 0 to 4.

2. The copolymer of claim 1 having from 15 to 25 parts of a member selected from the class consisting of acrylic or methacrylic acid.

3. The copolymer of claim 1 having from 75 to 85 parts of a member selected from the class consisting of lower alkyl acrylates and methacrylates.

4. The copolymer of claim 1 containing, in addition, from 5 to 20 parts, by volume, of an ester of acrylic acid or methacrylic acid, the alkyl group having from 8 to 18 carbon atoms.

5. The copolymer of claim 1 neutralized with ethylene imine.

* * * * *